United States Patent [19]
Becherer

[11] Patent Number: 5,964,265
[45] Date of Patent: Oct. 12, 1999

[54] VEHICLE TIRE WITH A DEVICE FOR DETERMINING TIRE-ROAD ADHESION

[75] Inventor: Thomas Becherer, Hannover, Germany

[73] Assignee: Continental Aktiengesellschaft, Hannover, Germany

[21] Appl. No.: 08/967,012

[22] Filed: Nov. 7, 1997

[30] Foreign Application Priority Data

Nov. 8, 1996 [DE] Germany .............................. 196 46 235

[51] Int. Cl.$^6$ .................................................. B60C 23/00
[52] U.S. Cl. ........................................................ 152/152.1
[58] Field of Search ............................... 152/154.2, 152.1

[56] References Cited

U.S. PATENT DOCUMENTS

| 5,483,827 | 1/1996 | Kulka et al. | 73/146.5 |
| 5,500,065 | 3/1996 | Koch et al. | 156/123 |

FOREIGN PATENT DOCUMENTS

| 3937966 | 5/1991 | Germany . |
| 3939917 | 6/1991 | Germany . |
| 4112738 | 10/1992 | Germany . |
| 4402136 | 7/1995 | Germany . |

OTHER PUBLICATIONS

Von Jörg Stöcker et al; Der . . . Forschungskooperation; 1995, pp. 824–832.

*Primary Examiner*—Francis J. Lorin
*Attorney, Agent, or Firm*—Robert W. Becker & Associates

[57] ABSTRACT

A vehicle tire for a motor vehicle has a carcass, a belt, and tire tread. A device for generating data for determining tire-road adhesion or friction between the footprint of the vehicle tire and the road surface is provided. The device includes at least one magnetic sensor connected to a evaluation device. The at least one magnetic sensor has individual magnetic sensor elements forming cooperating sensor element pairs. The device also includes a magnetic field arranged in the belt and generated during tire manufacture by partial magnetization of the belt. The at least one magnetic sensor is arranged in at least one lug of the tire tread.

4 Claims, 2 Drawing Sheets

VEHICLE TIRE WITH A DEVICE FOR DETERMINING TIRE-ROAD ADHESION

BACKGROUND OF THE INVENTION

The present invention relates to a vehicle tire, especially for motorized vehicles, with a device for generating data for further determination of actual frictional conditions between the footprint of the vehicle tire and the road surface on which the tire is running tire-road adhesion, whereby the device is substantially comprised of a plurality of individual magnetic sensor elements that cooperate with one another and a magnetic field positioned radially to the individual sensor elements. The magnetic sensors comprised of a group of individual sensor elements are connected to an evaluation device.

Such a vehicle tire is, for example, known from German patent 39 37 966. In this document a method for determining the frictional conditions (tire-road adhesion) between the vehicle tire and the road surface is disclosed whereby at one or more measuring locations within the tire local deformations, resulting within the footprint when the tire rolls on the road surface, are detected in a horizontal direction as well as in the normal direction at the footprint. Based on the localized deformations, the normal forces and the horizontal forces are determined and the frictional coefficient (tire-road adhesion coefficient) as a ratio of the horizontal force to the normal force is determined.

The friction between the vehicle tire and the road surface, i.e. the tire-road adhesion, ensures the transmission of acceleration forces and lateral guiding forces. The maximum frictional coefficient determines the limits of a stable driving behavior of the vehicle. Thus, it is important for maintaining a stable driving behavior, that the current frictional coefficient remains always below the maximum frictional coefficient. The frictional coefficient is the ratio of the horizontal forces, acting parallel to the road surface, to the vertically acting normal force. For assessing the frictional conditions in the circumferential direction of the tire and in the transverse direction, the frictional coefficient can be divided into a circumferential component, i.e., a longitudinal component, and a transverse component.

Due to the elasticity of the tire material the detected local deformations within the tire can provide data for the respective forces that cause this deformation. With sufficient precision it is thus possible to employ the forces introduced into the tire by the road surface for determining directly the frictional coefficient.

The prior art vehicle tire is provided in the area of the tread strip with at least one magnetic sensor which determines the local deformations and sends measured signals to an evaluation device via a corresponding signal transmission device. For the detection of the local horizontal or vertical stress, elongation, and deformations within the tread lug. Different constructive embodiments are disclosed with regard to the tire in German patent 39 37 966.

For example, permanent magnets are embedded within the tread lugs which change their position depending on the deformation caused by the road surface. Sensors may be connected to the belt ply which respond to the distance changes to the magnets. In this embodiment, the sensors must be securely connected to the belt because their position changes must be reproducible in a defined and reliable manner. The magnets within the tread lugs as well as the sensors within the belt, however, change their relative position during tire manufacture, especially during vulcanization and dishing. Since it is not predictable how this relative position of the two components will change within the finished tire, it is necessary to calibrate each finished tire. This requires high expenditures for their manufacture and the tires are correspondingly expensive. Also, errors made during calibration will make measured results useless.

According to a further embodiment, a sensor pin extends through the tire carcass into the tread lug of the tire tread. The sensor pin comprises four permanent magnets at its end projecting into the interior of the tire. These permanent magnets function as senders. The sensor housing is anchored with pins within the carcass and carries as receivers, for example, four Hall generators. The stress, elongations, and deformations cause a proportional pivoting, respectively, lifting movement of the sensor pin supported within the carcass and thus a distance change between the magnets, respectively, their magnetic field and the Hall generators. Thus, a change of the Hall voltage is the result which is transmitted as a measured signal to the evaluation device. This prior art tire, however, requires an even more expensive construction. Due to the magnets being embedded within the tread lug, whose movement must be detected by the Hall and/or magnetoresistive sensors, it is necessary to introduce at least two structural components into the tire. In addition to the costs for the respective components, the manufacture of the tire itself is also expensive.

It is therefore an object of the present invention to simplify the construction of the vehicle tire of the afore mentioned kind.

SUMMARY OF THE INVENTION

The vehicle tire for a motor vehicle according to the present invention is primarily characterized by:

A carcass, a belt, and a tire tread;

A device for generating data for determining friction between the footprint of the vehicle tire and a road surface;

The device comprising at least one magnetic sensor connected to an evaluation device;

The at least one magnetic sensor comprised of individual magnetic sensor elements forming cooperating sensor element pairs;

The device further comprising a magnetic field arranged in the belt and generated during tire manufacture by partial magnetization of the belt;

The at least one magnetic sensor arranged in at least one lug of the tire tread.

Advantageously, the belt comprises cords and the cords are magnetized.

The magnetic field is expediently generated by an induction coil.

The belt may contain a ferromagnetic powder for increasing magnetization of the belt.

Thus, according to the present invention, the sensors are arranged within at least one of the tread lugs and the magnetic field is arranged within the belt, whereby the magnetic field is generated by partial magnetization of the belt during tire manufacture.

With this design the magnetic field is thus moved into the belt ply. The belt ply within a finished tire is located at a reproducible position. The relative position of the sensors within the tread lug is therefore relatively unimportant because the force of the magnetic field can be adjusted to the position of the sensor. For example, it can be determined exactly by X-rays where the belt ply and where the sensors are located. By respectively magnetizing the belt, the tire is then finished. Since each tire can be individually magnetized, the complicated calibration is no longer necessary. The construction of the tire is substantially simplified because no expensive fixation of the sensors within the tread lug is required. Since less components are required in comparison to prior art tires, not only the weight of the tire is reduced, but also the manufacturing costs are reduced.

The metallic cords of the belt ply are magnetized. Accordingly, the material of the cords must be correspondingly selected. During manufacture, the magnetic field can be produced by using an induction coil.

A plurality of sensors and magnetic fields is distributed about the circumference of the tire in uniform spacing. The more sensors are provided, the more exact will be the measuring result.

For improving magnetization, the belt ply contains a ferromagnetic powder. This powder can be incorporated during manufacture into the rubber of the belt, for example, added during mastication of the rubber.

BRIEF DESCRIPTION OF THE DRAWINGS

The object and advantages of present invention will appear more clearly from the following specifications in conjunction with the accompanying drawings, in which.

DESCRIPTION OF THE PREFERRED EMBODIMENTS

Figure 1:
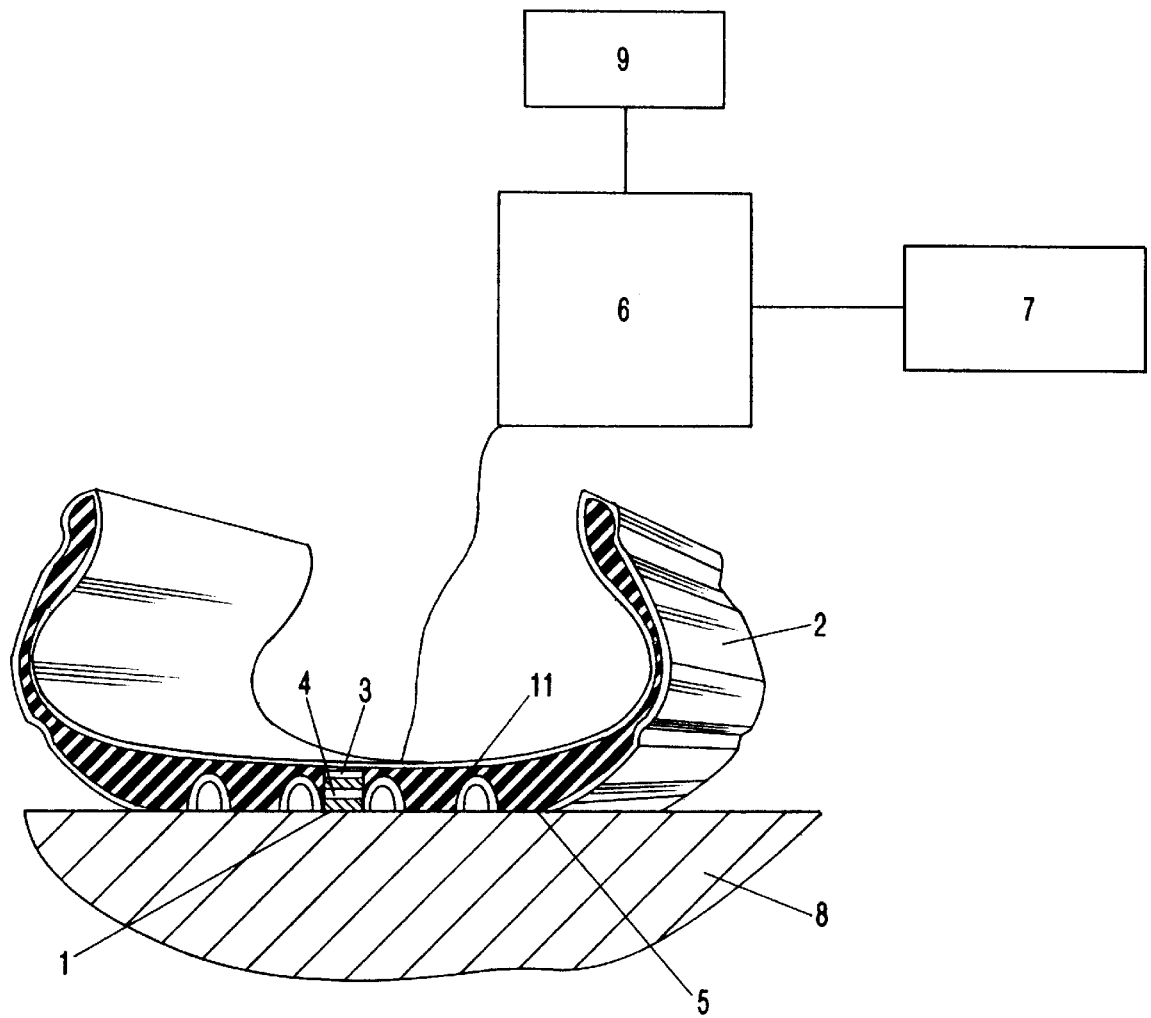
FIG. 1 shows a simplified representation of a vehicle tire in a part-sectional view with an evaluation device connected thereto.
Figure 2:
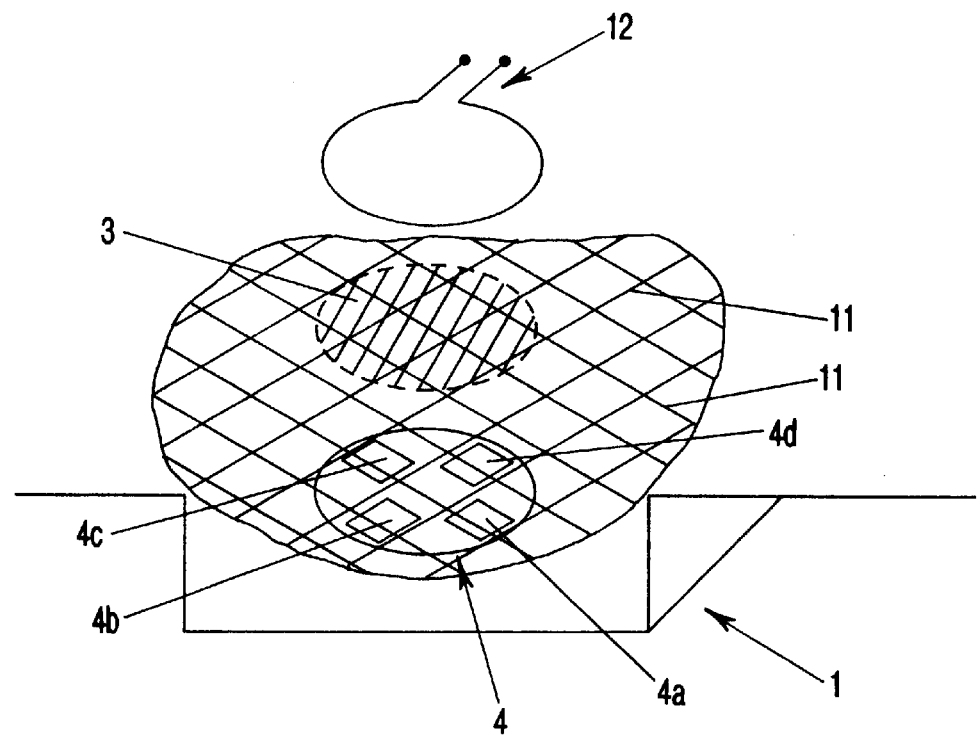
FIG. 2 is a symmetric representation of the sensor arrangement.
Figure 2:
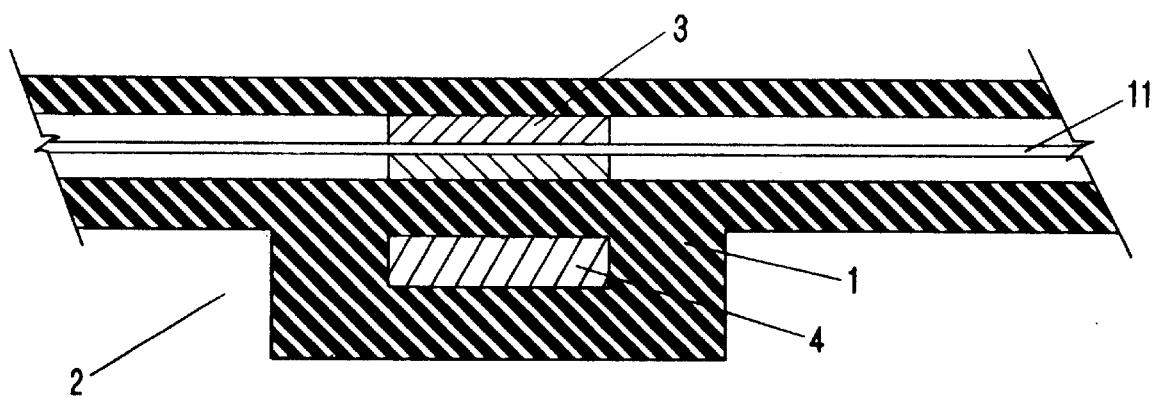

The present invention will now be described with the aide of several specific embodiments utilizing FIGS. 1 and 2.

A number of magnetic field sensors 4 are arranged within the tread lugs 1 of the tire 2 at uniform spacing in the circumferential direction. The sensors 4 are, for example, Hall sensors or magnetoresistive sensors which are comprised of four individual sensor elements 4a, 4b, 4c, 4d. Two sensor elements 4a, 4c; 4b, 4d are positioned opposite one another and form pairs. The sensors 4 are in communication with an evaluation device 6 which is connected, in turn, to an input device 7 and a display and/or alarm device 9. The area 13 of the belt 11 opposite the sensors 4 is magnetized. For this purpose, the steel cords within the belt 11 are partially magnetized during tire manufacturer by an induction coil 12. The connection of sensors 4 to the evaluation device 6 can be contactless, for example, can be performed inductively via a frequency-modulated signal or with rings. In the evaluation device 6 the timely course of the measured signals is assessed and the actually occurring frictional coefficient (tire-road adhesion) coefficient is determined within the footprint 5. The relative displacement or movement of the individual sensor elements, 4a, 4b, 4c, 4d to the magnetized area, 3 caused by stress within the circumferential direction, in the transverse direction, and in the vertical direction to the road surface, results in information in regard to the change of the spacial position and thus provides data in regard to the deformation within the footprint 5. In the evaluation device 6 the ratio of the actual frictional coefficient to the maximum frictional coefficient can be determined. When a maximum value, that has been entered via the input device, is surpassed, the driver will receive a signal from the display or alarm device 9 indicating to him that a critical driving condition is present. With respect further to method steps reference is made to the disclosure of German patent 39 37 966 which is incorporated herein by reference.

In order to increase or improve the magnetic field within the belt, a ferromagnetic powder can be incorporated into the rubber used for manufacturing the belt.

The present invention is, of course, in no way restricted to the specific disclosure of the specification and drawings, but also encompasses any modifications within the scope of the appended claims.

What is claimed is:

1. A vehicle tire for a motor vehicle comprising:

a carcass, a belt, and a tire tread;

a device for generating data for determining friction between a foot print of said vehicle tire and a road surface;

said device comprising at least one magnetic sensor connected to an evaluation device;

said at least one magnetic sensor comprised of individual magnetic sensor elements forming cooperating sensor element pairs;

said device further comprising a magnetic field for each one of said magnetic sensors, wherein said magnetic field is arranged in said belt and generated during tire manufacture by partial magnetization of said belt opposite said at least one magnetic sensor in a radial direction of said vehicle tire;

said at least one magnetic sensor arranged in at least one lug of said tire tread.

2. A vehicle tire according to claim 1, wherein said belt comprises cords and wherein said cords are magnetized.

3. A vehicle tire according to claim 1, wherein said magnetic field is generated by an induction coil.

4. A vehicle tire according to claim 1, wherein said belt contains a ferromagnetic powder for increasing magnetization of said belt.

* * * * *